United States Patent
Fercher

(10) Patent No.: US 7,695,140 B2
(45) Date of Patent: Apr. 13, 2010

(54) FOURIER-DOMAIN OCT RAY-TRACING ON THE EYE

(75) Inventor: Adolf Friedrich Fercher, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 372 days.

(21) Appl. No.: 11/658,821

(22) PCT Filed: Jul. 26, 2005

(86) PCT No.: PCT/EP2005/008090
§ 371 (c)(1),
(2), (4) Date: Jan. 26, 2007

(87) PCT Pub. No.: WO2006/015717
PCT Pub. Date: Feb. 16, 2006

(65) Prior Publication Data
US 2008/0284981 A1    Nov. 20, 2008

(30) Foreign Application Priority Data
Aug. 3, 2004   (DE) .................. 10 2004 037 479

(51) Int. Cl.
*A61B 3/10* (2006.01)
(52) U.S. Cl. .................. 351/221; 351/246; 351/210
(58) Field of Classification Search ................... 351/221
See application file for complete search history.

(56) References Cited

U.S. PATENT DOCUMENTS

| | | | |
|---|---|---|---|
| 5,909,270 A * | 6/1999 | Moser et al. .......... | 351/212 |
| 6,268,921 B1 | 7/2001 | Seitz et al. | |
| 6,377,349 B1 | 4/2002 | Fercher | |
| 6,556,853 B1 * | 4/2003 | Cabib et al. .......... | 600/407 |
| 7,355,716 B2 * | 4/2008 | de Boer et al. .......... | 356/479 |

(Continued)

FOREIGN PATENT DOCUMENTS

DE        43 09 056        9/1994

(Continued)

OTHER PUBLICATIONS

Navarro and Losada "Aberrations and relative efficiency of light pencils in the living human eye", *Optometry and Vision Science* 74(7), 540-547, 1997.

(Continued)

*Primary Examiner*—Jessica T Stultz
(74) *Attorney, Agent, or Firm*—Eugene LeDonne; Joseph W. Treloar; Frommer Lawerence & Haug LLP

(57) ABSTRACT

The present invention is directed to an ophthalmologic measurement method which can depict three-dimensional structures of the interfaces of an eye by short-coherence interferometry based on reference points. For this purpose, the pupil is illuminated at a plurality of points by a short-coherence illumination source. The measurement beam reflected at these points by the interfaces and surfaces of the eye is superimposed with a reference beam. The measurement data which are generated in this way are spectrally split by a diffraction grating, imaged on a two-dimensional detector array and conveyed to a control unit which determines a three-dimensional structure of all intraocular interfaces and surfaces of the eye. In the suggested Fourier domain OCT method, the depiction of three-dimensional structures is preferably carried out by spline surfaces or polygon surfaces. In doing so, it is possible to determine the depth positions of the measurement beams in many points of the pupil with a single recording of the array camera in that the pupils are illuminated by a diaphragm grid and the reference mirror contains a periodic phase grid.

10 Claims, 7 Drawing Sheets

U.S. PATENT DOCUMENTS

| | | | |
|---|---|---|---|
| 7,364,296 B2 * | 4/2008 | Miller et al. | 351/206 |
| 7,404,640 B2 * | 7/2008 | Ferguson et al. | 351/221 |
| 2003/0038921 A1 * | 2/2003 | Neal et al. | 351/212 |

FOREIGN PATENT DOCUMENTS

| | | |
|---|---|---|
| DE | 101 42 001 | 3/2003 |
| WO | WO 03/062802 | 7/2003 |
| WO | WO 2004/043245 | 5/2004 |

OTHER PUBLICATIONS

Navarro and Moreno-Barriuso "Laser ray-tracing method for optical testing", *Optics Letters* 24(14), 951-953, 1999.

G. Häusler and M. W. Lindner for producing OCT images "Coherence RADAR" and "spectral RADAR"—New Tools for dermatological diagnosis, *J. Biomed.* Opt. 3(1), 21-31, 1998.

XP 002272406—Maciej Wojtkowski, et al. "In vivo human retinal imaging by Fourier Domain Optical Coherence Tomography", Journal of Biomedical Optics, Jul. 2002 vol. 3, No. 3, pp. 457-463.

XP 002350079—Andres F. Zuluaga, et al. "Spatially Resolved Spectral Interferometry For Determination Of Subsurface Structure", Optics Letters, Apr. 15, 1999, vol. 24, No. 8, pp. 519-521.

XP 002350080—Robert J. Zawadzki, et al. "Three-dimensional ophthalmic optical coherence tomography with a refraction correction algorithm", Proc. Of SPIE, vol. 5140, No. 1, pp. 20-27, 2003.

XP 002350082—Enrique Corona, et al. "Digital Stereo Image Analyzer for Generating Automated s-D Measures of Optic Disc Deformation in Glaucoma", IEEE Transactions on Medical Imaging, Oct. 2002, vol. 21, No. 10, pp. 1244-1253.

A. F. Fercher et al. "Measurement of optical distances by optical spectrum modulation", *Proc. SPIE* vol. 2083, 263-267, 1993.

Bellingham, W. A., "In Vivo Optical Coherence Tomography in Ophthalmology", *SPIE*, pp. 355-370, ISBN 0-8194-1379-8,1993.

A. G. Podoleanu, J. A. Rogers, D. A. Jackson, and S. Dunne "Three dimensional OCT Images from retina and skin", *Opt. Express* 7, pp. 292-298, 2000.

S. Radhakrishnan et al. "Real time optical coherence tomography of the anterior segment using hand-held and slit-lamp adapted systems", *Proc. SPIE* 4619, 227-229, 2002.

Chapter: "Optical Coherence Tomography in Medicine" in vol. 4 of the series "Optical Sciences: International Trends in Optics and Photonics ICO IV" published 1999, Springer Verlag, Berlin, editor: T. Asakura, pp. 359-389.

A. F. Fercher et al. "Measurement of Intraocular Distances by Backscattering Spectral Interferometry", *Opt Commun.* 117, 43-48, 1995.

* cited by examiner

FOURIER-DOMAIN OCT RAY-TRACING ON THE EYE

CROSS-REFERENCE TO RELATED APPLICATIONS

This application claims priority of International Application No. PCT/EP2005/008090, filed Jul. 26, 2005 and German Application No. 10 2004 037 479.1, filed Aug. 3, 2004, the complete disclosures of which are hereby incorporated by reference.

BACKGROUND OF THE INVENTION a) Field of the Invention

The present invention is directed to a measuring method for ophthalmology which uses short-coherence interferometry to measure the positions of reference points on the basis of which the three-dimensional structure of all refracting and reflecting intraocular interfaces and surfaces can be depicted, for example, by means of spline surfaces or polygon surfaces.

b) Description of the Related Art

For this purpose, measurement beams are radiated into the eye simultaneously through a number of pupil points, and the depth positions at which these measurement beams pierce or are reflected at intraocular interfaces and surfaces are determined by spectral short-coherence interferometry (also known as Fourier domain OCT). Based on these piercing points and reflection points, the shape of these surfaces can be calculated numerically and used for depicting the structure of the eye in three dimensions by means of known computer graphics techniques such as spline surfaces or polygon surfaces.

For this purpose, the object to be measured is placed in one arm of a two-beam interferometer. The spectrum of the light bundle coming from the measured object is superimposed with the reference bundle at the interferometer output and the resulting spectral intensity is evaluated by spectrometry.

Roughly over the last 15 years, various experimental ray tracing methods have been developed which are suitable for measuring the characteristics of optical systems. For example, Navarro and Losada ("Aberrations and relative efficiency of light pencils in the living human eye", *Optometry and Vision Science* 74(7), 540-547, 1997) illuminate the pupil of the eye with parallel laser beams and determine the imaging characteristics of the eye from the position of the remitted beam on the photocathode of a CCD camera which is conjugated to the retina with respect to imaging. The application of this method for measuring the imaging characteristics of optics is described by Navarro and Moreno-Barriuso ("Laser ray-tracing method for optical testing", *Optics Letters* 24(14), 951-953, 1999). However, in this ray tracing method the cumulative total effect of all refracting surfaces is measured. The determination of the shape of individual interfaces and, therefore, a causal relationship between aberrations of the eye and the causative interfaces can only be approximated.

At present, ray tracing is known chiefly as a computer graphics method for depicting realistic illumination conditions in three-dimensional reproduction (rendering) of computer images. However, ray tracing, along with wavefront tracing, is also a numerical process for calculating the light propagation in inhomogeneous media. Whereas ray tracing, which is based on the laws of refraction, is already used in optics for optical design, the application of wavefront tracing, which is based on Huygens' principle, is known rather in seismology for calculating the propagation of seismic waves.

In optical coherence tomography, images are generated from short-coherence interferometric measurement data of so-called A-scans. These A-scans determine the object structure as a distribution of light-remitting points along the measurement beams in the depth of the object. The light remitted by the object is correlated with a reference beam in the short-coherence interferometer by displacing the reference mirror. On the other hand, according to the known rules of Fourier domain OCT, the A-scan data are calculated by Fourier transformation of the intensity spectra of the light that is remitted by the object and superimposed with a reference beam (Bouma, B. E., Tearney, G. J., Handbook of Optical Coherence Tomography", Marcel Dekker Verlag, New York, chapter 12, 2002).

For purposes of ray tracing in the eye it is necessary to illuminate the pupil of the eye at a plurality of distributed pupil points and to evaluate the measurement beams in a corresponding manner. In known time domain OCT, a pupil scan in which the measurement beam is guided consecutively to the various pupil points by a scanning unit is required for this purpose. The intensity spectrum of the A-scan would have to be measured at every point. This is time-consuming and can lead to motion artifacts.

For this purpose, a superluminescent diode, a light-emitting diode (LED), a mode-lock laser, an ASE (Amplified Spontaneous Emission) fiber light source, a photonic crystal fiber light source, a thermal light source (incandescent lamp), or a plasma light source (arc lamp), for example, can be used as a short-coherence illumination source.

Similar optical Fourier OCT methods which are known from the art will first be discussed in the following.

Publications by A. F. Fercher et al. ("Measurement of optical distances by optical spectrum modulation", *Proc. SPIE* Vol. 2083, 263-267, 1993) describe the optical Fourier OCT method in general and also the specific determination of the coherence function of the light reflected by the eye through inverse Fourier transformation of the spectral intensity distribution $I(\omega)$ ("In Vivo Optical Coherence Tomography in Ophthalmology", Bellingham, W. A., *SPIE*, pp. 355-370, ISBN 0-8194-1379-8, 1993).

The use of Fourier transform methods specifically for measuring intraocular distances along an individual beam through the pupil was described by A. F. Fercher et al. ("Measurement of Intraocular Distances by Backscattering Spectral Interferometry", *Opt. Commun.* 117, 43-48, 1995) and used by G. Häusler and M. W. Lindner for producing OCT images ("Coherence RADAR" and "spectral RADAR"—New Tools for dermatological diagnosis", *J. Biomed*. Opt. 3(1), 21-31, 1998).

DE 43 09 056 A1 describes a method for determining the distance and scattering intensity of scattering points in which the distance and the local scattering intensity are determined by Fourier transformation of the spectrum according to wavelength.

A method in which three-dimensional images of the retina can be synthesized from en-face OCT recordings was described by A. G. Podoleanu, J. A. Rogers, D. A. Jackson, and S. Dunne ("Three dimensional OCT Images from retina and skin", *Opt. Express* 7, pp. 292-298, 2000).

A parallel OCT method which likewise uses a step reference mirror is described in U.S. Pat. No. 6,268,921 B1. The step reference mirror is used to implement the depth scan in time domain OCT. Accordingly, the step sizes are also appreciably greater than $\lambda/8$. Further, the steps are distributed over the entire surface in a staircase shape rather than with periodically recurring total heights. The phase shifter used in this solution acts identically on the entire reference arm or measurement arm. These differences are a natural result of the different problem to be solved as stated therein.

A similar method which is based on piezoelectric phase shifting phase measurement is disclosed in U.S. Pat. No. 6,377,349 B1. In this solution, the displacement of the reference mirror is effected by means of piezo electricity. However, this displacement, the required additional exposures and the repeated readout of the photodetector array require time which leads to motion artifacts in in vivo objects like the eye.

A conventional OCT method for determining the dimensions of the anterior segments of the eye using a slit lamp and a hand-held device was described by S. Radhakrishnan et al. ("Real time optical coherence tomography of the anterior segment using hand-held and slit-lamp adapted systems", Proc. SPIE 4619, 227-229, 2002). The device which is based on time domain OCT works very fast and delivers eight images per second. For example, the eight images per second can be distributed equidistantly on the entire pupil for a three-dimensional depiction of the anterior eye structure; about one second would then be required for data recording. In contrast, the method upon which the present application is based can register the required data within milliseconds.

OBJECT AND SUMMARY OF THE INVENTION

Therefore, the primary object of the present invention is a very fast measurement of reference points for the three-dimensional depiction of the structure of refracting and reflecting intraocular interfaces and surfaces by means of spline surfaces or polygon surfaces.

According to the invention, this is carried out by means of Fourier domain distance measurement simultaneously in many measurement beams distributed over the pupil of the eye.

In the Fourier domain ray tracing in the eye according to the invention, the pupil is illuminated by a short-coherence illumination source at a plurality of points with measurement beams penetrating into the eye, and the measurement radiation reflected by interfaces and surfaces of the eye at the piercing points of the measurement beams is superimposed on a reference beam. At the output of the interferometer, the measurement beam which is superimposed with the reference beam is split spectrally, e.g., by a diffraction grating, and imaged on a two-dimensional detector array. The resulting electric signals are conveyed to a control unit. This control unit determines the position of the above-mentioned piercing points along the measurement beams by means of Fourier transformation. These piercing points form the reference points for the depiction of the three-dimensional structure of all refracting and reflecting intraocular interfaces and surfaces of the eye.

The invention will be described in more detail in the following with reference to embodiment examples. The description refers to a Michelson interferometer, but other types may also be used.

DESCRIPTION OF THE PREFERRED EMBODIMENTS

Figure 1:
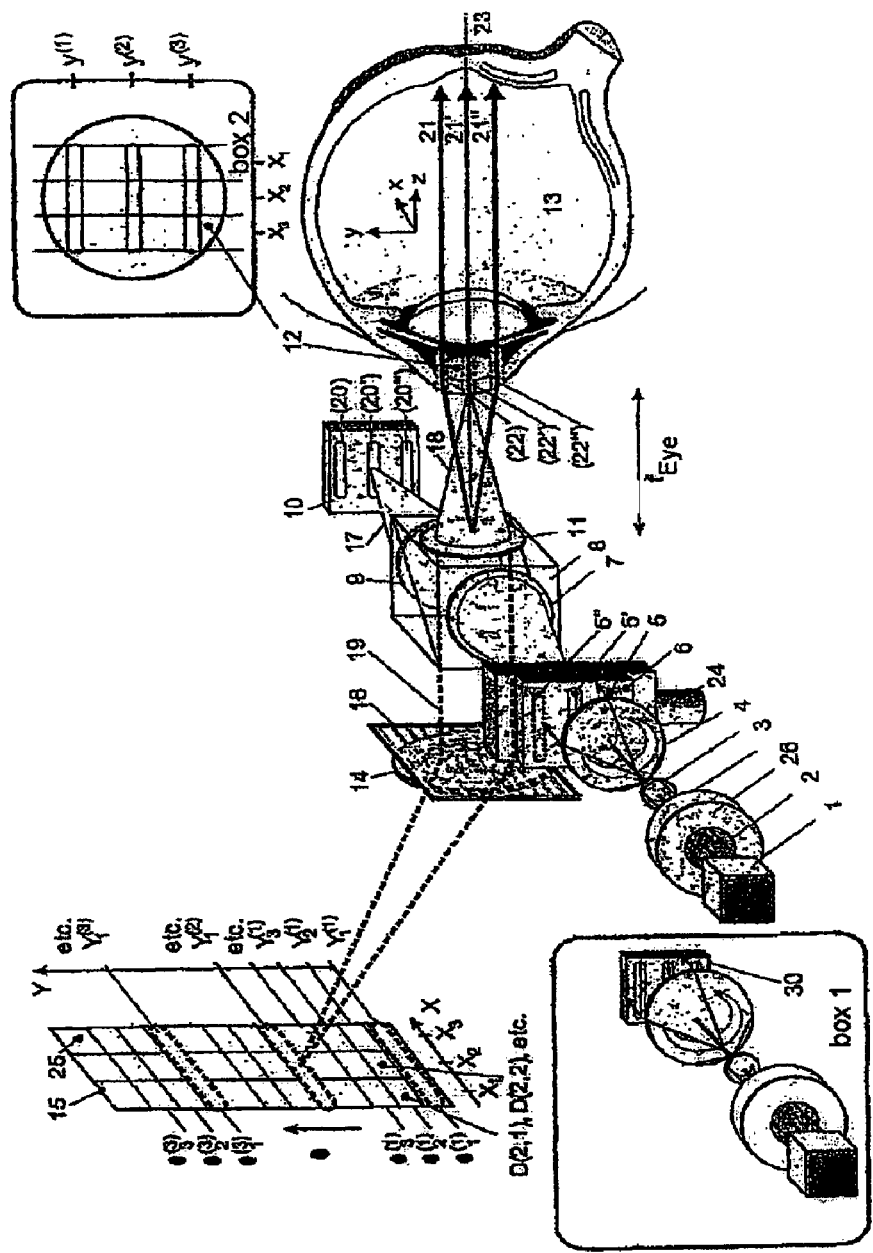
FIG. 1 shows a short-coherence interferometer according to the invention with measurement beams impinging divergently on the pupil.

FIG. 1 shows a short-coherence interferometer according to the invention for ray tracing with divergent illumination of the eye. In this case, the light beam 2 which is emitted by the short-coherence illumination source 1 and passes through the shutter 26 illuminates, via optics 3 and 4, a light slit opening 5 which is moved in y-direction by a drive unit 24. The light slit diaphragm 6 can also have a series of openings instead of a slit. The light slit of the light slit diaphragm 6 is moved consecutively into positions 5, 5' and 5". The optics 7 image the light slit opening on the reference mirror 10 through the beamsplitter 8 by optics 9 on one side and on the pupil 12 of the eye 13 via the splitter surface of the beamsplitter 8 by optics 11 on the other side. The light slit images 20, 20' and 20" corresponding to the different positions 5, 5' and 5" of the light slit diaphragm 6 on the reference mirror 10 and 22, 22' and 22" in the pupil 12 of the eye 13 are imaged by optics 11, 9 and 14 on the detector array 15 in positions $Y_j(1), Y_j(2)$ and $Y_j(3)$, where $j=1, 2, 3, \ldots$.

Optics 14, the detector array 15 and the diffraction grating 16 form a spectrometer which spectrally analyzes the intensity spectrum of the light beam 19 exiting from the short-coherence interferometer after the beamsplitter 8 in direction of the detector array 15. The light beam 19 comprises the object beams 18 and reference beams 17 which are reflected so as to be superimposed on one another.

The detectors 25 of the detector array 15 are arranged in columns with identical X-values $X_1, X_2$, etc. and in rows with identical Y-values $Y_j^{(k)}$, where j corresponds to the wavelength number and k corresponds to the light slit number.

While recording data, the light slit of the light slit diaphragm 6 is driven by a motor 24 so as to be displaced in y-direction consecutively in positions 5, 5', 5" etc. so that the pupil 12 is illuminated consecutively by light slit images 22, 22' and 22" and the reference mirror 10 is illuminated consecutively by light slit images 20, 20' and 20" in corresponding y-positions $y^{(1)}, y^{(2)}$ and $y^{(3)}$.

The light beams 19 formed by the superposition of the reference beams 17 and the object beams 18 generate light slit images with superimposed reference radiation on the detector array 15 in positions $Y_j^{(1)}, Y_j^{(2)}, Y_j^{(3)}$. Detector rows on which the column spectrum is dispersed lie between positions $Y_j^{(1)}, Y_j^{(2)}, Y_j^{(3)}$ on the detector array 15. The positions $(x_i; y^{(k)})$ on the pupil 12 correspond to the positions $(X_i; Y_j^{(k)})$ on the detector array 15, where "j" designates the spectral components.

The dispersion of the diffraction grating 16 distributes the spectral components of the light beam 19 from positions $y^{(k)}$ to wavelengths $\lambda_1^{(k)}, \lambda_2^{(k)}$, etc. As is illustrated in box 2 in FIG. 1, the spectral intensity $I_i^{(k)}(\lambda_j)$ in position $(X_i; \lambda_j^{(k)})$ for $j=1, 2, 3, \ldots$ at the detector array 15 belongs to a point $(x_i; y^{(k)})$ in the pupil 12. The spectral intensities $I_i^{(k)}(\lambda_j)$ which are measured in this case by the detectors 25 in column (for respective constant i) $X_i$ and rows $Y_j^{(k)}$ for $k=1, 2, \ldots$ depending on the wavelength $(\lambda_j^{(k)})$ form the data for the Fourier transformation for calculating the object structure according to the rules of Fourier domain OCT. The wavelength-dependent measurement data must be recalculated to wave number dependency for this purpose. The z-coordinates of the reference points are then determined by Fourier transformation along a measurement beam in the image-conjugated pupil positions $x_j$, $y^{(k)}$ at the eye 13.

The diffraction grating 16 required for the dispersion of the light beam 19 can also be constructed as a reflection grating or as a dispersion prism.

There are two basic modes for reading out the spectrum. In both modes, the shutter 26 is always open only when the light slit is in positions 5, 5', 5", etc. In the simultaneous mode, the spectra of all of the light slit positions are electronically read out simultaneously. For this purpose, the intensity values occurring from the different slit positions are initially stored at the array. The detector rows lying between the $Y_1^{(k)}$ positions are available for spectral resolution and, therefore, for depth resolution. This mode can be very fast because of the simultaneous readout of the entire spectrum. However, the field depth is limited by the limited quantity of detector rows lying between the $Y_1^{(k)}$ positions.

In the consecutive mode, on the other hand, the spectra are read out immediately when the light slit is in positions 5, 5', 5", etc. However, this mode is slower than the simultaneous mode because the readout process, which is required here much more frequently, operates with a delay. Of course, the consecutive mode has the advantage that appreciably more detector rows (e.g., all those above position $Y_1^{(i)}$) are available for the $\lambda$ spectrum.

It should be noted that the method according to the invention is described herein only for three columns ($X_1$, $X_2$ and $X_3$) and three rows ($Y_1^{(1)}$, $Y_1^{(2)}$ and $Y_1^{(3)}$). The method can be implemented for any numbers of columns and rows, these numbers being limited by the numbers of columns and rows of the detector array 15.

In addition to time delays due to the readout process of the detector array 15, the scanning movement of the light slit also takes time. This time delay can be prevented by means of a light slit grid. As is shown in box 1 of FIG. 1, the light beam 2 exiting from the short-coherence illumination source 1 now illuminates a light slit grid 30 via optics 3 and 4.

Further imaging of the light slit grid 30 is carried out corresponding to the solution described in the preceding in connection with the light slit diaphragm 6 which is moved by a motor 24 and which has only one light slit. In this case also, the light slit images 20, 20', 20" on the reference mirror 10, 22, 22' and 22" in the pupil 12 of the eye 13 and $Y^{(1)}$, $Y^{(2)}$ and $Y^{(3)}$ on the detector array 15 correspond to the different positions of the light slit of the light slit grid 30.

In the beam path shown in FIG. 1, the optics 11 are located in the front focal plane of the eye 13. The pupil 12 is accordingly illuminated by divergent measurement beams 21, 21' and 21" whose divergence center lies in the front principal focus of the eye 13. As is indicated in FIG. 1, these measurement beams are directed in parallel from the optics (cornea and lens) of the eye 13.

Figure 2:
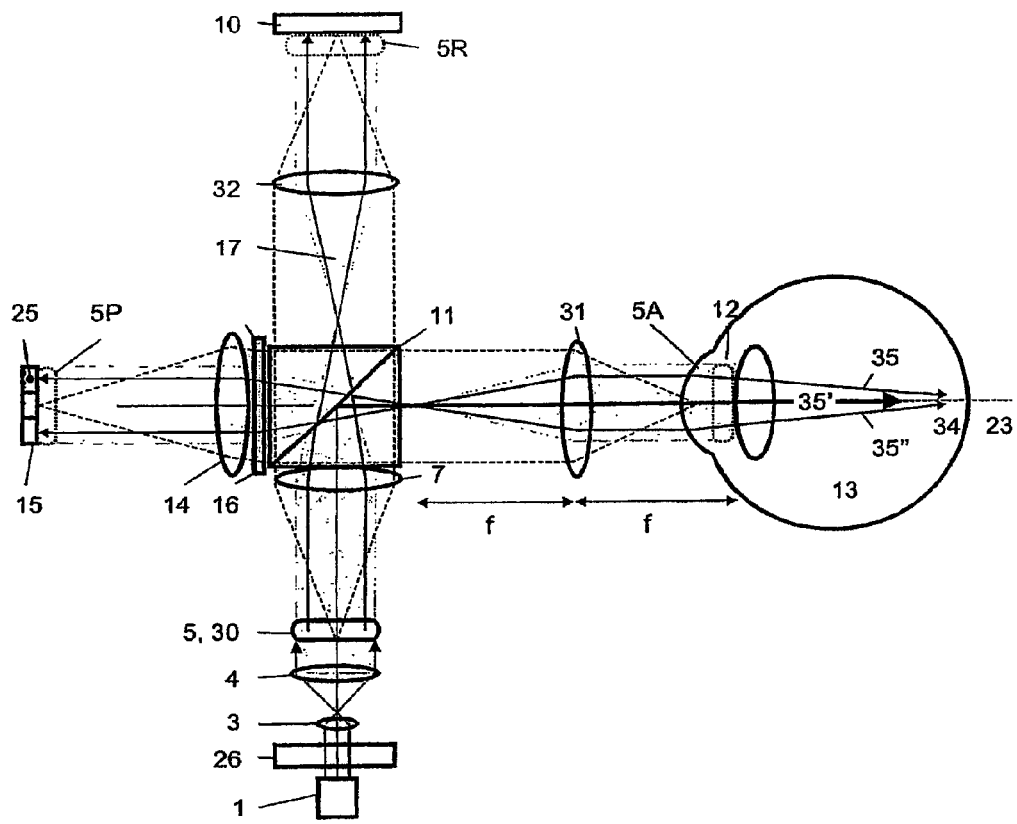
FIG. 2 shows a short-coherence interferometer according to the invention with measurement beams impinging in parallel on the pupil.

Alternatively, the pupil 12 of the eye 13 can be illuminated by parallel measurement beams as is shown in FIG. 2. With parallel illumination, the light slit of the light slit diaphragm 6 or of the light slit grid 30 is initially imaged at infinity by the optics 7 and after the beamsplitter 11 is focused by the optics 32 on the reference mirror 10 and by optics 31 on the pupil 12.

The most important difference between the two illumination variants consists in the beam path inside the eye 13. While the measurement beams 21, 21' and 21" in the divergent illumination according to FIG. 1 can acquire an approximately cylindrical volume, the measurement beams (35, 335' and 35") with parallel illumination converge in the eye 13. They are focused on the fundus of the eye by the (relaxed) eye 13 corresponding to the normal line of sight.

Figure 3:
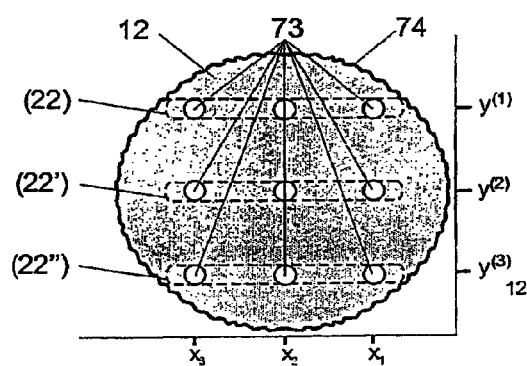
FIG. 3 shows the image of the iris 74 with pupil points 73.

The arrangements described above suffer from the drawback that the depth measurement area is appreciably reduced when there is a large quantity of measurement beams because then there is a lower number of pixels. For purposes of illustration, FIG. 3 shows a grid of 3×3 pupil points 73 inside the iris 74. The light slit images 22, 22' and 22" in the pupil 12 are shown for illumination with a light slit diaphragm 6 or a light slit grid 30. For example, in ray tracing measurement at 10×10 pupil points 73 at the detector array 15, since the pupil 12 is imaged on the detector array 15 only 1/10 of the detectors 25 of the total columns of the detector array 15 which are associated with the respective x-position of the pupil point (x, y) are still available. The field depth is accordingly reduced to 1/10 of the maximum possible value. Therefore, for a CCD camera with approximately 2000 detectors, there is a field depth of around 10 mm which is sufficient for the anterior chamber in most cases. However, with 10×10 measurement beams through the pupil, this field depth is reduced to about 1 mm, which is hardly enough for measuring the cornea thickness.

Figure 4:
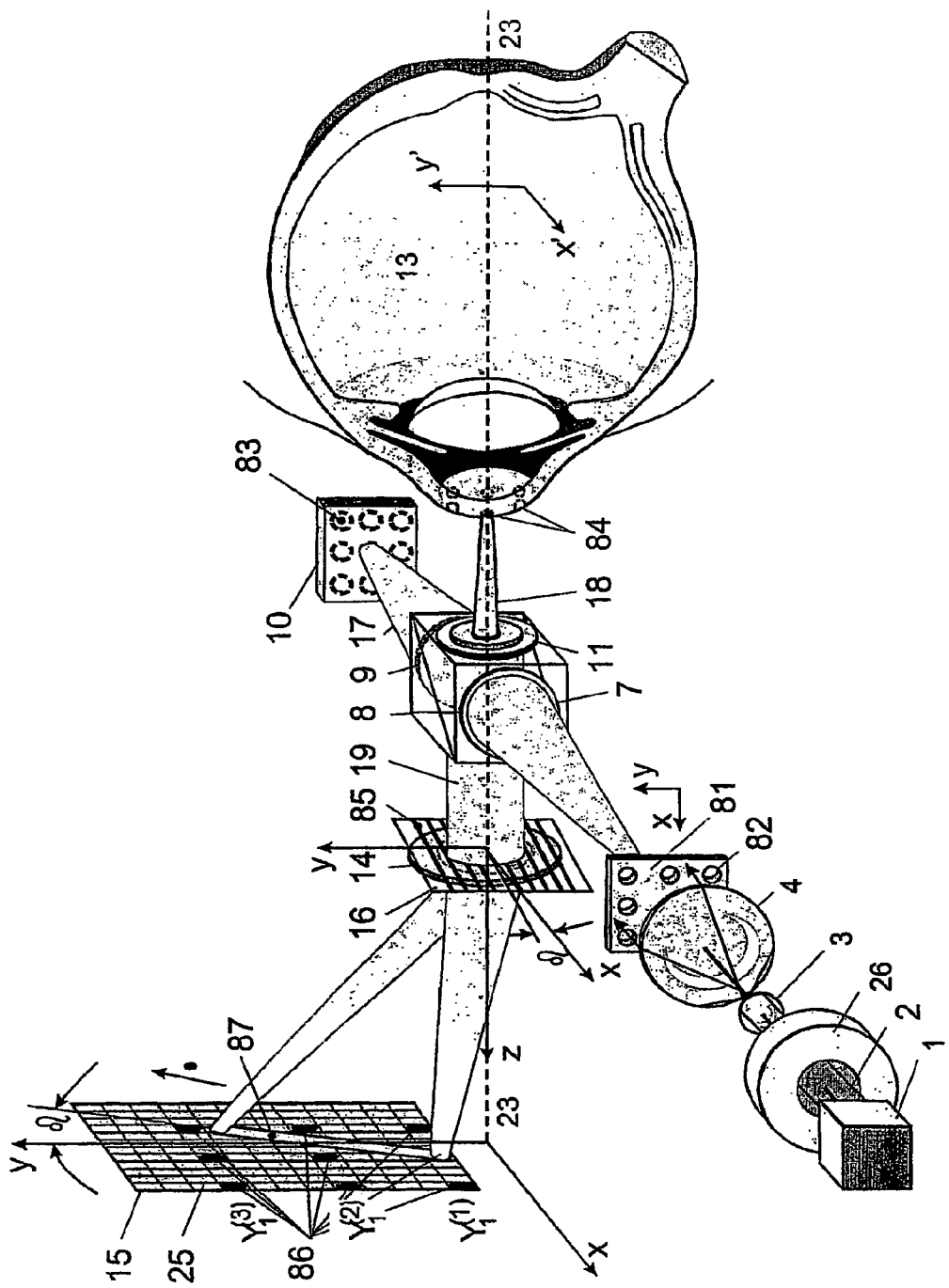
FIG. 4 shows a short-coherence interferometer according to the invention with a diffraction grating 16 that is rotated by angle $\beta$.

Another constructional variant of a short-coherence interferometer for ray tracing is shown in FIG. 4. In this variant, a higher resolution can be achieved by rotating the diffraction grating by angle β.

According to FIG. 4, the light beam 2 which is emitted by the short-coherence illumination source 1 and passes through the shutter 26 illuminates, via optics 3 and 4, the diaphragm grid 81 with the diaphragm openings 82 which in this case are arranged, for example, in three rows in x-direction and three columns in y-direction.

The diaphragm grid 81 is imaged on the reference mirror 10 through the beamsplitter 8 by optics 7 and 9 and is imaged on the pupil 12 of the eye 13 by optics 7 via the splitter surface of the beamsplitter 8 by optics 11. The diaphragm image 83 on the reference mirror 10 and the diaphragm image 84 on the eye 13 are imaged on the detector array 15 by optics 11, 9 and 14 through the diffraction grating 16. The optics 14, the detector array 15 and the diffraction grating 16 form the spectrometer which spectrally analyzes the intensity spectrum of the light beam 19. The light beam 19 comprises the superimposed reference beams 17 and the object beams 18 of all diaphragm openings 82. The diffraction grating 16 disperses the spectral components of the light beam 19 in direction normal to the grating lines 85.

In this case also, the spectrometric intensities measured in y-direction at the detector array 15 columnwise depending on the wavelength form the output data for the Fourier transformation for calculating the object structure along measurement beams in the x'- and y'-positions at the eye 13. In spectrometry, the diffraction grating 16 is usually oriented in such a way that its grating lines 85 are oriented normal to the y-direction of the (one-dimensional) detector array 15 (parallel to the x-direction) because the spectral resolution would otherwise be worsened. The arrangements described herein are likewise based on this orientation of the diffraction grating 16.

The light beams 19 formed as a result of the superposition of the reference beams 17 and the object beams 18 generate light slit images on the detector array 15 in positions $Y_1^{(1)}$, $Y_1^{(2)}, Y_1^{(3)}, Y_2^{(1)}, Y_2^{(2)}, Y_2^{(3)},$ and $Y_3^{(1)}, Y_3^{(2)}, Y_3^{(3)}$. Only the detectors 25 of the respective column lying between positions $Y_1^{(1)}$ and $Y_1^{(1)}$ are available for the spectral resolution. The detectors 25 of the other columns are not used.

By rotating the diffraction grating 16 by the azimuthal angle β, the wavelength-dependent dispersion of the light bundle 19 is now carried out as a spectrum 87 in a direction that is inclined by the azimuthal angle β relative to the y-axis. The available area on the detector array 15 for the spectrum 87 can be increased in this way. The diffraction grating 16 is rotated in such a way that its grating lines 85 enclose an azimuthal angle β (in the x-y plane) with the x-axis.

Figure 5:
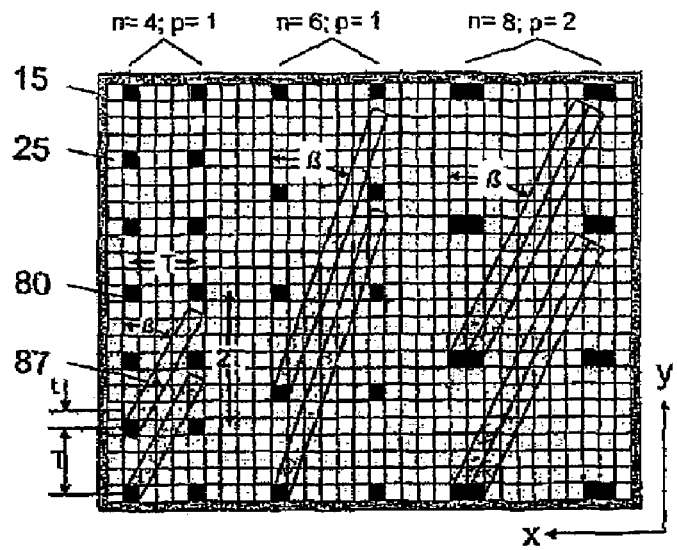
FIG. 5 illustrates the gain in spectral resolution that can be achieved by rotating the diffraction grating 16.

FIG. 5 shows a detector array 15 with different imaging patterns for the light beams 19. The detector array 15 comprises N times N (for example, where N=2048) square detectors 25. In the detectors 80 marked in black, the shortest wavelength of the spectrum 87 is imaged, for example.

In the left-hand third of FIG. 5, n=4 detectors 25 are accounted for in a division T of the diaphragm grid and n=6 are accounted for in the middle third. The grating dispersion must now disperse the other wavelengths in such a way that spectra of neighboring diaphragm points do not impinge on the same detectors 25. As can be seen from FIG. 5, tan $$\beta = \frac{n}{n \cdot n/2} = \frac{2}{n}.$$

When the diffraction grating 16 is rotated by the azimuthal angle β, there are approximately n=2/tan β detectors 25 available for resolving the spectrum and the field depth can accordingly be significantly increased.

This condition applies strictly only under the assumption that the sensitive regions of the detectors 25 directly adjoin one another, which is substantially the case in CCD arrays. Further, the spectra 87 of the individual diaphragm openings 82 may not exceed the width of the detectors 25. Otherwise, the angle β must be increased correspondingly and the spectral resolution is somewhat worse. On the other hand, when zones which are not sensitive to light are located between the detectors 25, the angle β estimated above can also be greater and the resolution can accordingly be further improved.

The azimuthal angle β between the measurement beam grid or diaphragm grid 81 and the diffraction grating 16 is crucial. Irrespective of this, the detector array 15 can be rotated in different directions. For example, it may be useful to rotate the detector array 15 by angle β also. The spectra 87 of the measurement beams then impinge on the detectors 25 of an individual array column, which can simplify the readout process.

The arrangements described above were based on conventional Fourier domain OCT which, as is well known, supplies extensive autocorrelation terms in addition to the desired object structure, so that the imaging depth of Fourier domain OCT is limited.

It is already known that autocorrelation terms can be avoided when a plurality of intensity spectra with different phases of the reference beam are measured. In this connection, reference is had to the chapter "Optical Coherence Tomography in Medicine" in Volume 4 of the series "Optical Sciences: International Trends in Optics and Photonics ICO IV" (published 1999, Springer Verlag, Berlin, editor: T. Asakura, pages 359-389). For this purpose, a plurality of spectral intensity measurements must be carried out, and the path lengths of the reference waves between the individual measurements must be changed by fractions of a light wavelength.

Figure 6:
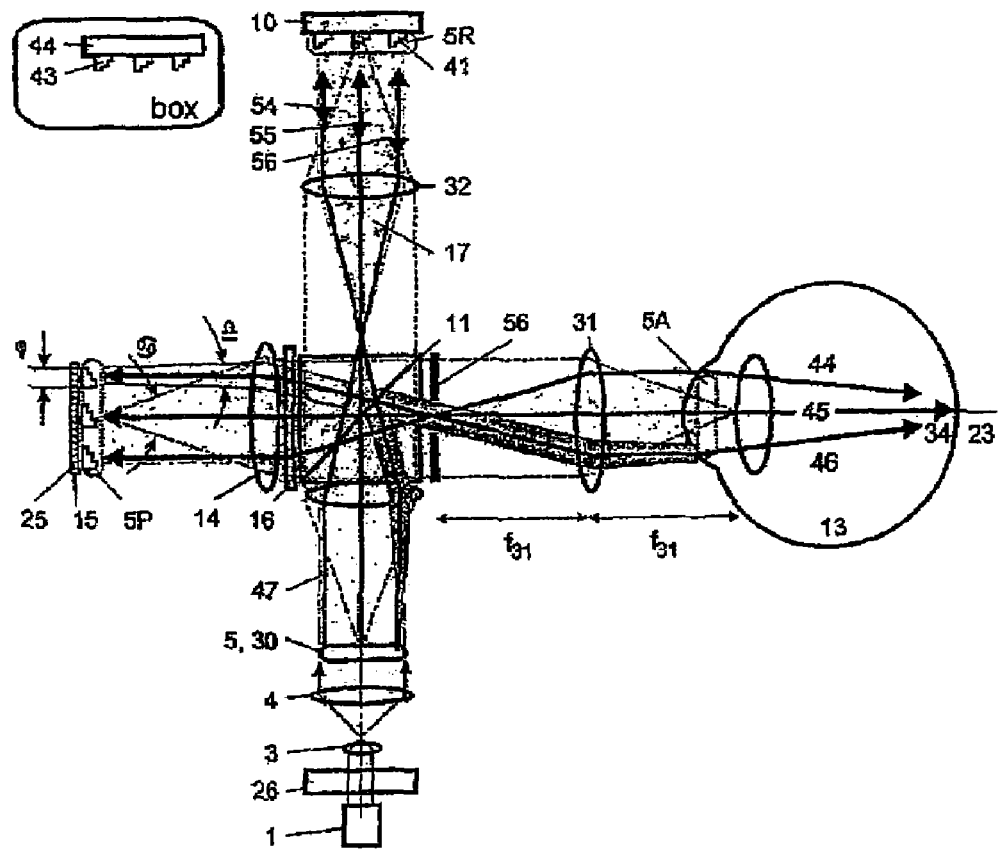
FIG. 6 shows a phase multiplexing short-coherence interferometer according to the invention.

FIG. 6 shows the beam path of an OCT device which is based on the phase multiplexing Fourier domain technique.

In contrast to the arrangements described in the preceding, a reference mirror 10 having a step-shaped reflected phase profile on its mirror surface is used in this case. This phase profile comprises a periodic arrangement of phase staircases 41 with two or more steps. The step heights are smaller than a light wavelength.

Alternatively, a transparent phase profile can also be provided. In this case, the phase staircases are arranged as transparent layers of corresponding thickness on a transparent plate which is arranged in the beam path between the beamsplitter 11 and reference mirror 10.

The phase profile comprises periodically arranged staircases with a few steps which are smaller than λ. In FIG. 6, the phase staircase comprises, for example, three steps which have a step height of λ/8. The corresponding reference beams 54, 55 and 56 with associated phase staircase belong to the three measurement beams 44, 45 and 46.

The measurement beams and reference beams can also be part of an individual wide interferometer beam bundle. While the reference beams 54, 55 and 56 image the phase steps on the detector array 15 in transversal resolution because of the large aperture (aperture angle α) in the reference beam path, the measurement beams 44, 45, and 46 are defocused virtually on an entire phase staircase because of the smaller aperture in the measurement beam path (aperture angle δ) that is limited by the pinhole diaphragm 56. Accordingly, the intensity values associated with the different reference phases can be read out separately on the detector array 15 for every measurement beam.

The pinhole diaphragm 56 can be used at the same time to limit the energy flux density of the illuminated beam to the value permissible for the eye 13.

When there are three phase steps per measurement beam, the luminous flux that is available per phase measurement is reduced by a factor of three. Accordingly, there is a formal reduction of 5 dB in the signal-to-noise ratio and a gain in measurement time by a factor of 3. However, since the eye can also be loaded by a higher radiation output within a shorter measurement time, the gain in measurement time is not at all bound to a loss in the signal-to-noise ratio.

Further, no reference mirror movements are required and the readout is carried out only once (one-shot recording) so that the advantages with respect to time are appreciably greater than the factor of 3.

Figure 7:
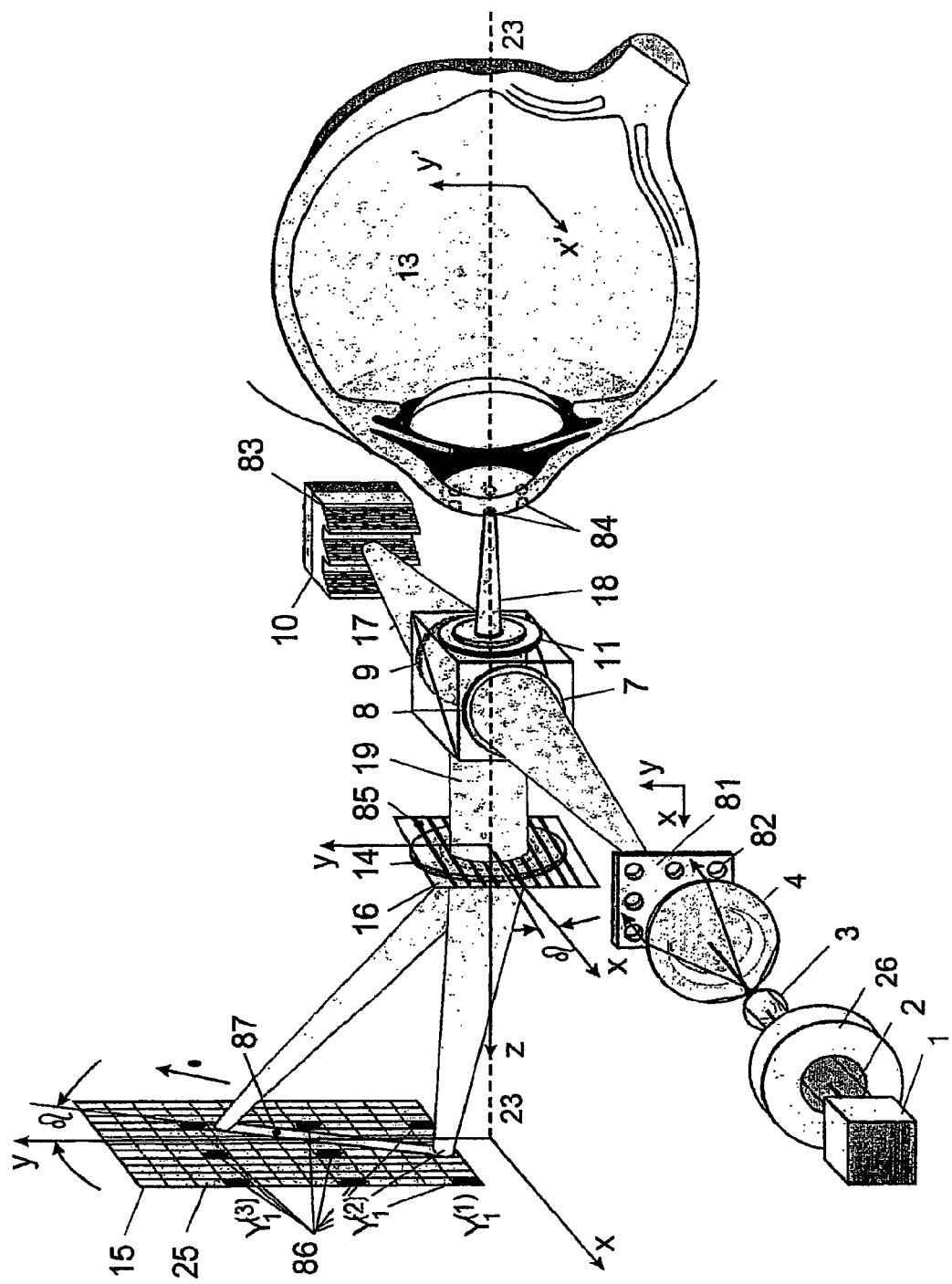
FIG. 7 shows a phase multiplexing short-coherence interferometer according to the invention in which the diffraction grating is rotated by angle $\beta$.

FIG. 7 shows the beam shape of an arrangement for phase multiplexing Fourier OCT in which the diffraction grating is rotated by angle β.

In this solution, the light beam 2 which is emitted by the short-coherence illumination source 1 and passes through the shutter 26 illuminates, by optics 3 and 4, a diaphragm grid 81 with the diaphragm openings 82 which are arranged symmetrically, for example, in three rows and three columns in this case.

The diaphragm grid 81 is imaged by optics 7 and 9 through the beamsplitter 8 on the reference mirror 10 with the phase profile 83 on one side and by the optics 7 via the surface of the beamsplitter 8 by optics 11 on the pupil of the eye 13 on the other side. The diaphragm image 83 on the reference mirror 10 and the diaphragm image 84 on the eye 13 are imaged on the detector array 15 by optics 11, 9 and 14 through the diffraction grating 16. The optics 14, the detector array 15 and the diffraction grating 16 form the spectrometer which spectrally analyzes the intensity spectrum of the light beam 19. The light beam 19 comprises the superimposed reference beams 17 and object beams 18 of all of the diaphragm openings 82. The diffraction grating 16 disperses the spectral components of the light beam 19 in direction normal to the grating lines 85.

In this case also, the spectrometric intensities measured in y-direction at the detector array 15 columnwise depending on the wavelength form the output data for the phase multiplexing Fourier transformation for calculating the object structure along measurement beams in the x'- and y'-positions at the eye 13.

By rotating the diffraction grating 16 by the azimuthal angle β, the wavelength-dependent dispersion of the light bundle 19 is now carried out as a spectrum 87 in a direction that is inclined by the azimuthal angle β relative to the y-axis. The available area on the detector array 15 for the spectrum 87 can be increased in this way.

In Fourier domain OCT ray tracing in the eye, according to the invention, the pupil 12 of the eye 13 is illuminated by a short-coherence illumination source 1 at a plurality of points. There are several conceivable variants for the diaphragm arrangement that is used. For one, a pinhole diaphragm can be used which illuminates the eye at different points one after the other, or a slit diaphragm is used which need only be moved in one direction over the eye. Further, it is also possible to use diaphragm grids which have diaphragm openings or diaphragm slits and illuminate all points at once. Another variant is to use so-called lens grids.

The use of a moving light diaphragm will be discussed in more detail in the following. The light slit can be displaced consecutively into the measurement positions, for example, by means of a stepping drive.

Figure 8A:
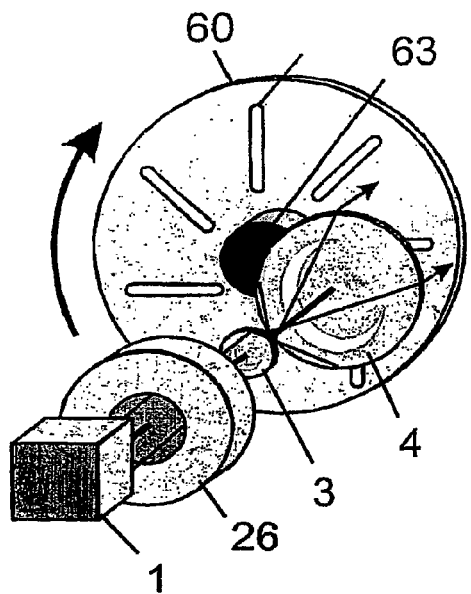
FIGS. 8a and 8b show arrangements of slit diaphragms on a rotating disk.
Figure 8B:
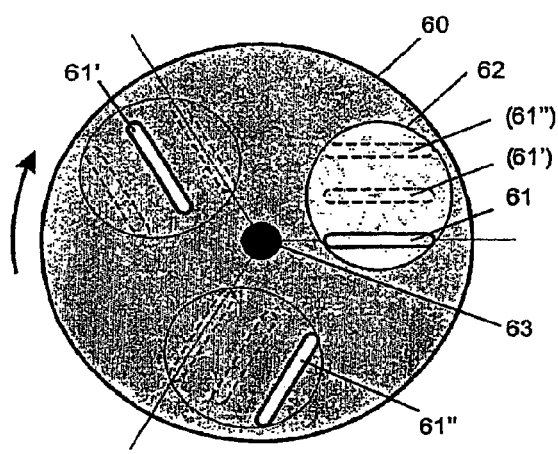

Further, it is also possible to use a rotating diaphragm arrangement. FIG. 8a shows the arrangement of slit diaphragms on a rotating disk 60. However, because of the orthogonal arrangement of the detectors 25 in the detector array 15, only one individual light slit opening 61 may be oriented exactly in radial direction on this disk as is illustrated by the three light slit openings 61, 61' and 61" distributed along the circumference of the disk 60. During a revolution of the disk 60, A-scan measurements are carried out in the image-conjugated eye pupil 62 in the three light slit positions 61, 61' and 61". The quantity of light slit openings 61 arranged on the disk 60 can vary.

Figure 9:
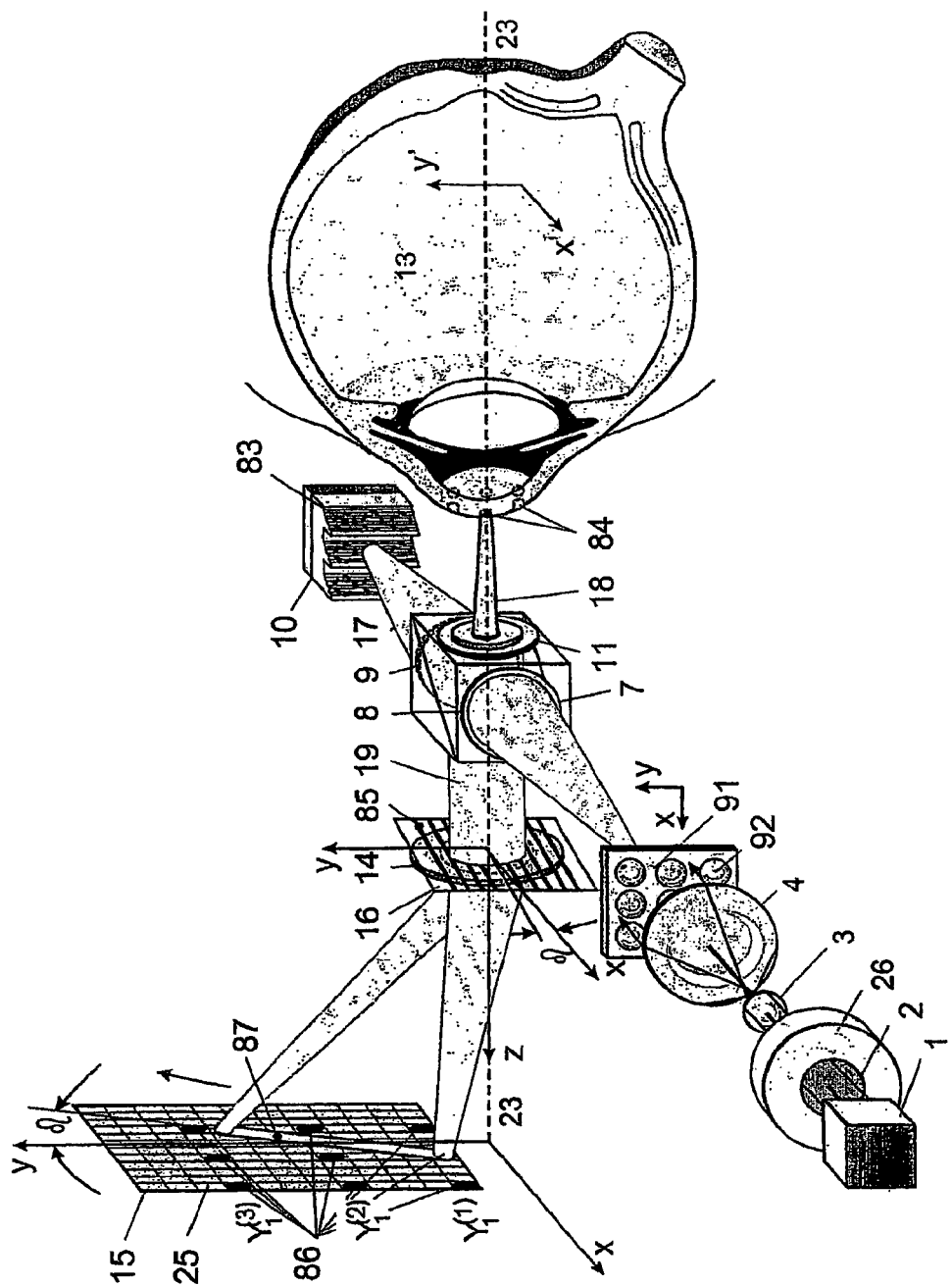
FIG. 9 shows a phase multiplexing short-coherence interferometer according to the invention with a lens raster in the illumination beam of the interferometer.

Finally, a lens grid 91 can be used instead of the diaphragm grid 81 as is shown in FIG. 9. This lens grid 91 has an appreciably greater etendue compared to the diaphragm grid 81. The lens grid 91 is likewise illuminated through optics 3 and 4 by the light beam 2 which is emitted by the short-coherence illumination source 1 and which passes through the shutter 26. The focal points of the individual lenses 92 of the lens grid 91 take the place of the diaphragm openings 82, for example, in the arrangement according to FIG. 7.

In the Fourier domain OCT method according to the invention, the depiction of a three-dimensional structure of all refracting and reflecting intraocular interfaces and surfaces of the eye is preferably carried out by means of spline surfaces or polygon surfaces.

With the proposed method it is possible to determine the depth positions of the piercing points and reflection points of the measurement beams at many points of the pupil with an individual recording of the array camera. This can be achieved in that the pupil is illuminated by a diaphragm grid and the reference mirror contains a periodic phase grid. The method delivers excellent image quality with a large object depth.

Further, Fourier domain OCT ray tracing at the eye can be substantially improved. For one, the resolving capacity is substantially improved by rotating the diffraction grating by an angle. Through the use of diaphragm grids or lens grids, it is possible to substantially reduce the measuring time by one-shot methods and accordingly to prevent motion artifacts. The present solution is based on the physical principles of spectral amplitude measurement and phase measurement modified for Fourier domain OCT. Thanks to a reference beam with spatially periodic phase scanning, it is no longer necessary to displace the reference mirror in different positions.

While the foregoing description and drawings represent the present invention, it will be obvious to those skilled in the art that various changes may be made therein without departing from the true spirit and scope of the present invention.

What is claimed is:

1. A method for obtaining a Fourier domain OCT ray tracing at an eye comprising the steps of:
   illuminating a pupil of the eye at a plurality of reference points by a short-coherence illumination source and superimposing a measurement beam reflected at the reference points by interfaces and surfaces of the eye with a reference beam;
   spectrally splitting measurement data of the reference points at an output of an interferometer and imaging the measurement data on a two-dimensional detector array for the simultaneous readout of two-dimensional spectral-interferometric data and two-dimensional spatial data at the output of the interferometer; and
   conveying the measurement data to a control unit which determines the depiction of a three-dimensional spatial structure of all refracting and/or reflecting intraocular interfaces and surfaces of the eye based on the reference points which have been determined by spectral interferometry.

2. The fourier domain OCT ray tracing method according to claim 1;
   wherein a moving diaphragm opening, a diaphragm grid, or a lens grid is used for illuminating the pupil at a plurality of points.

3. The fourier domain OCT ray tracing method according to claim 1;
   wherein a diffraction grating is provided for spectrally splitting the measurement data at the output of the interferometer and can be constructed as a transmission grating or reflection grating.

4. The fourier domain OCT ray tracing method according to claim 3;
   wherein an increased resolution can be achieved in Fourier domain OCT by introducing an azimuthal angle β≠0 between the light beam exiting from the beam interferometer and the diffraction grating.

5. The fourier domain OCT ray tracing method according to claim 4;
   wherein the azimuthal angle β introduced between the light beam and the diffraction grating for increasing the resolution in Fourier domain OCT is preferably $$\tan\beta = \frac{n}{n \cdot n/2} = \frac{2}{n},$$

where n is the quantity of detectors per division of a diaphragm grid.

6. The fourier domain OCT ray tracing method according to claim 1;
   wherein a reference mirror for generating a reference beam with a periodic phase profile has a step-shaped phase profile whose step heights are less than the wavelength of the short-coherence illumination source.

7. The fourier domain OCT ray tracing method according to claim 6;
wherein the step-shaped phase profile of the reference mirror has one, two, or more phase steps and can be constructed as a reflecting or transparent surface profile.

8. The fourier domain OCT ray tracing method according to claim 5;
wherein the azimuthal angle β introduced between the light beam and the diffraction grating for increasing the resolution in Fourier domain OCT is preferably $$\tan\beta = p\frac{2}{n},$$

where n is the quantity of detectors per division of the diaphragm grid and p is the quantity of measurement data sets with different reference phases.

9. The fourier domain OCT ray tracing method according to claim 4;
wherein the two-dimensional detector array is preferably likewise rotated by the azimuthal angle β so that the spectra of the measurement beams impinge on the detector array in direction of the detector columns.

10. The fourier domain OCT ray tracing method according to claim 1;
wherein the depiction of a three-dimensional structure of all refracting and reflecting intraocular interfaces and surfaces of the eye is carried out by means of spline surfaces or polygon surfaces.

* * * * *